United States Patent [19]

Yuki et al.

[11] Patent Number: 4,666,633
[45] Date of Patent: May 19, 1987

[54] PROCESS FOR PREPARING TRIARYLMETHYL METHACRYLATE

[75] Inventors: Yoichi Yuki, Himeji; Ryoji Noyori, Aichi; Masahiko Hayashi, Nagoya, all of Japan

[73] Assignee: Daicel Chemical Industries, Ltd., Sakai, Japan

[21] Appl. No.: 639,969

[22] Filed: Aug. 10, 1984

[30] Foreign Application Priority Data

Aug. 17, 1983 [JP] Japan .................................. 58-150038

[51] Int. Cl.[4] ........................ C09B 11/06; C07C 67/10
[52] U.S. Cl. ..................................... 260/395; 260/386; 560/235; 560/236
[58] Field of Search ................ 260/395, 386; 560/235, 560/236

[56] References Cited

U.S. PATENT DOCUMENTS

| 3,931,290 | 1/1976 | Bourgau et al. | 560/236 |
| 4,375,495 | 3/1983 | Yuki et al. | 428/402 |

FOREIGN PATENT DOCUMENTS

| 2024948 | 1/1971 | Fed. Rep. of Germany | 560/236 |
| 53-108914 | 9/1978 | Japan | 560/236 |
| 56-106907 | 8/1981 | Japan | 428/402 |
| 57-130945 | 8/1982 | Japan | 428/402 |
| 278674 | 7/1969 | U.S.S.R. | 560/236 |

OTHER PUBLICATIONS

Calmon & Kressman, *Ion Exchangers in Organic and Biochemistry*, 1957, pp. 22–23.
N. A. Adrova and L. K. Prokhorova, Vysokomolekulyarnye Soedineniya 3, 1509 (1961).
Chemical Abstracts, vol. 56, Cols. 10383 and 10384.

*Primary Examiner*—Glennon H. Hollrah
*Assistant Examiner*—Raymond Covington
*Attorney, Agent, or Firm*—Flynn, Thiel, Boutell & Tanis

[57] ABSTRACT

A triarylmethyl methacrylate is produced by reacting methacrylic acid with a triarylmethylating agent in an inert, organic solvent containing therein an excess amount of an amine or in the presence of an anion exchanger.

5 Claims, No Drawings

PROCESS FOR PREPARING TRIARYLMETHYL METHACRYLATE

According to the invention a triarylmethyl methacrylate is produced by reacting methacrylic acid with a triarylmethylating agent in an inert, organic solvent containing therein an excess amount of an amine or in the presence of an anion exchanger. The process can be carried out effectively in the industrial point of view. The product as obtained in the process is useful as a starting monomer to produce a polymer having optical resolving power. The use of the product is disclosed in Japanese patent publication (unexamined) No. 106907/1981.

Heretofore, triphenylmethylation reaction has been utilized in most cases for protecting carboxyl groups of synthetic intermediates, so that it has been applied to various acids. Since formed triphenylmethyl esters merely served as intermediates, there have been scarcely any problems in the separation and purification of the esters. In the production of the above-mentioned monomer, wherein the acid component is restricted to methacrylic acid, however, it is industrially important to efficiently isolate highly pure esters while preventing them from being polymerized and hydrolyzed.

It is generally known that triphenylmethyl esters of carboxylic acids are liable to undergo rapid hydrolysis and hence it is impossible to obtain these esters by the dehydration reaction between an acid and an alcohol. Heretofore, triphenylmethyl esters have been prepared by reacting triphenylmethyl chloride or bromide with a metal salt of a carboxylic acid in a non-polar solvent. Particularly when esterifying an acid liable to undergo a side reaction, for example, methacrylic acid liable to undergo polymerization, the reaction had to be carried out by using an expensive silver salt as represented by the reaction formula (1):

(1)

wherein Tr represents a triphenylmethyl group.

This reaction is fully described in the literature (N. A. Adrova and L. K. Prokhorova, Vysokomolekulyarnye Soedineniya 3, 1509 (1961)). This method using an equivalent of silver has problems from the viewpoints of economy and natural resources.

As the process for producing triphenylmethyl methacrylate using no silver salt, only a process using trialkylsilyl esters as proposed by some of the present inventors (Japanese Patent Laid-Open No. 130945/1982) is known.

It is an object of the present invention to provide a process for easily producing esters by starting with methacrylic acid in the form of free acid without using methacrylic acid in the form of a metal salt such as silver salt as in the prior art process mentioned above. In the process of the present invention, side reactions hardly take place, the obtained products can be easily separated and pure esters can be obtained by merely recrystallizing the crude products and therefore the process of the present invention can dispense with purifying treatments by, for example, chromatography which sometimes causes hydrolysis.

It is another object of the present invention to provide an industrial process which can be easily carried out and gives the desired products in high purity from an easily available starting material without the necessity of recovering expensive silver or using starting materials which are difficult to obtain.

The invention provides a process for producing a triarylmethyl methacrylate of the formula:

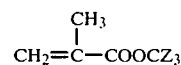

in which Z is an aryl group, which comprises the step of reacting methacrylic acid with a triarylmethylating agent of the formula:

$$Z_3CX$$

in which X is a group eliminatable due to the nucleophilicity of methacrylic acid, in an inert, organic solvent containing therein an excess amount of an amine or in the presence of an anion exchanger.

The invention as defined above has two preferable embodiments. One is a process as defined as above in which Z is an unsubstituted or substituted phenyl group and the reaction is conducted in an inert, organic solvent containing therein an excess amount of an amine, in the meantime or after the reaction removing the precipitated amine salt, evaporating the solvent and the excess amine from the resulting solution. The other is a process as defined above in which the reaction is carried out in the presence of an anion exchanger. Each of these embodiments of the invention will be illustrated below.

First Embodiment of the Invention

In the present invention, methacrylic acid per se is used as the carboxylic acid component for producing esters and is reacted with a compound having a triphenylmethyl structure, such as triphenylmethyl bromide or chloride. Among the metal salts of methacrylic acid, only silver salt has heretofore been successful in the production of triphenylmethyl methacrylate which is liable to be polymerized or hydrolyzed. We have succeeded in condensing a polymerizable carboxylic acid with an easily hydrolyzable triphenylmethyl compound by using an amine in place of the metal salt. This reaction is carried out in an inert organic solvent to avoid hydrolysis.

The present invention is characterized not only in that there is provided a method of condensation using an inexpensive amine in place of conventional expensive silver salt, but also in that a far simplified separating and purifying method is realized.

For this purpose, a volatile amine such as triethylamine is used in excess of methacrylic acid. The excess amine accelerates the condensation reaction and at the same time prevents the reaction system from being shifted to an acidic pH region. Though the reaction is carried out while inhibiting the incorporation of water in the reaction system, a trace amount of water is inevitably incorporated therein so that a prolonged reaction time and particularly a shift of the pH to an acidic range are deleterious, since the intended product of the present invention undergoes hydrolysis. When the reaction is carried out while paying attention to the inhibition of the above-mentioned phenomenon, an amine salt such as triethylamine hydrobromide is precipitated in a relatively short time, for example, within two or three hours and the reaction is terminated. The desired triphenylmethyl methacrylate can be directly crystallized by removing the amine salt by filtration and evaporating the solvent and the excess amine from the resulting reaction solution. If desired, the purity can be further improved by conventional techniques such as recrystallization.

The above-described simple method of obtaining the desired products in a high purity has been realized because:

(1) triphenylmethyl methacrylate per se has good crystallizability;

(2) the reaction was carried out in the presence of an excess amine so that side reactions such as hydrolysis could be perfectly prevented from taking place; and (3) the starting materials were chosen in such a manner that the materials (amine salt and excess amine) coexisting with the product when the reaction was terminated could be removed by quite simple means such as filtration and evaporation. These countermeasures are peculiar to the process of the present invention.

When acetic or acrylic acid is used in place of methacrylic acid to carry out the reaction in a similar manner to that of the present invention, triphenylmethyl esters can be produced indeed, but none of them are so pure nor directly crystallizable as the corresponding methacrylate. When benzoic acid is used, the reaction rate is slow as compared with methacrylic acid, and even when the reaction time is prolonged, there can not be obtained large crystals as in the case of the methacrylate. TLC analysis revealed that triphenylmethyl alcohol and benzoic acid, both having high crystallizability, were incorporated.

Starting Material

The reaction of the present invention can be represented by the following reaction formula (2):

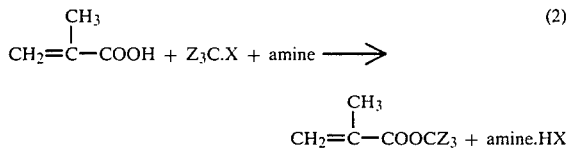

wherein Z is an unsubstituted or substituted phenyl group, and three Z groups may be the same or different. The Z group can be represented by the following formula:

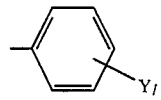

wherein a substituent Y is an alkyl group ($C_1$-$C_{20}$), an alkoxy group ($C_1$-$C_{20}$) or a halogen atom (F, Cl, Br or I), and l is an integer of 0 to 5. Among these substituents, p-chloro and p-fluoro groups can be mentioned as typical halogen substituents. Preferred alkyl groups include $C_1$-$C_{10}$ alkyl groups, particularly m-methyl, 3,5-dimethyl and m-ethyl groups. Preferred alkoxy groups include $C_1$-$C_{10}$ alkoxy groups, particularly m-methoxy, 3,5-dimethoxy and m-ethoxy groups.

X is a group which can be easily eliminated due to the nucleophilicity of methacrylic acid. Examples of the substituent X include halogen,

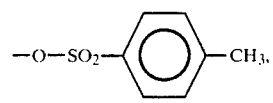

—O—$SO_2$—$CH_3$ —, $ClO_4$, —CN and —SCN.

Typical compounds of the formula $Z_3CX$ include triphenylmethyl chloride and triphenylmethyl bromide, but triphenylmethyl derivatives having substituted phenyl groups as exemplified above and triphenylmethyl derivatives having other eliminatable groups can be similarly used in the process of the present invention.

Reaction Conditions

Usually, the reaction is carried out in an inert organic solvent. A solvent which does not dissolve the formed amine salt is used. The solvent to be used must be anhydrous, since when the solvent contains water, the resulting ester is liable to undergo hydrolysis. Examples of typical solvents include paraffin hydrocarbons such as n-pentane and n-hexane; aromatic hydrocarbons such as benzene and toluene; halogenated hydrocarbons such as dichloromethane and carbon tetrachloride; acetonitrile and ethers such as; diethyl ether and tetrahydrofuran (THF).

Preferred amines used in the present invention include tertiary amines which are inert to the starting materials. However, primary and secondary amines may be used unless side reactions such as N-triphenylmethylation reaction take place under reaction conditions. It is desirable that the amine salt formed by the reaction is easily precipitated and can be filtered off from the organic solvent.

It is necessary that the amine is used in excess of methacrylic acid, i.e., in at least equimolar quantities to that of methacrylic acid. The amine is usually used in a quantity of 1.5 to 10 times by mol that of methacrylic acid, whereby the reaction can be terminated in a short time and the reaction system can be prevented from being shifted due to an acidic pH. A volatile amine is preferably used, because excess amine must be removed together with the solvent by evaporation after the removal of the amine salt by filtration. For the purpose of the present invention, triethylamine is particularly preferred, because it is easy to handle as a liquid, can be easily removed by evaporation, is inert to the starting material and has an appropriate basicity. Alkylamines having 12 or less carbon atoms in total such as trimethylamine, tributylamine or diisopropylamine, may also be used, but have advantages and disadvantages in respect of volatility or the like.

Even when a weak base such as pyridine is used, the amine salt can be precipitated from the reaction solution. Since, however, pyridine hydrobromide is acidic, the desired ester is liable to be hydrolyzed by a trace amount of water contained in the solution. Therefore, trialkyl-amines or amines having a similar basicity to them are preferred.

The reaction can be carried out at about room temperature or while cooled with ice. If desired, the reaction can be carried out over a wide temperature range of, for example, −80° to 100° C., unless any problems of side reactions such as polymerization are caused. Cooling (for example, to 10° to 20° C.) is often effective in accelerating the precipitation of the amine salt, and the reaction and the precipitation of the amine salt can be completed within 6 hours, for example, after 2 to 3 hours.

The precipitated amine salt can be easily removed by conventional solid-liquid separation methods such as filtration, and the solvent and excess amine are evaporated from the mother liquor. If necessary, the removal of the solvent and excess amine is carried out under reduced pressure. Triphenylmethyl methacrylate can be obtained directly as a crystal. If desired, the purity can be further improved by conventional techniques such as recrystallization.

In this way, the present invention succeeds in obtaining the desired products in a crystalline form by a method wherein a triphenylmethyl ester is formed from methacrylic acid in a short time without using methacrylic acid or a particular derivative thereof and the formed ester is recovered by such simple separation means as filtration and evaporation.

Second Embodiment of the Invention

Commercially available methacrylic acid containing a polymerization inhibitor can be used as such.

The term "triarylmethylating agent" used herein refers to all compounds, such as triphenylmethyl chloride, conventionally used, and is represented by the formula, $Z_3CX$, wherein X is an atom or an atom group which can be easily eliminated as an anion due to the nucleophilicity of methacrylic acid. Examples of the substituent X include halogen atoms, $-O-SO_2C_6H_4CH_3$, $-OSO_2CH_3$, $-ClO_4$, $-CN$ and $-SCN$.

Z is an aryl group such as phenyl, α-naphthyl or β-naphthyl, which may be substituted with 1 to 5 groups, such as halogen (F, Cl, Br, or I), alkyl, alkoxy or alkenyl, which are inert to the reaction of the present invention. Particularly useful Z groups include a phenyl group and substituted phenyl groups having a substituent Yl represented by the formula:

wherein l is an integer of 1 to 5 and Y is a halogen atom such as p-chloro or p-fluoro, an alkyl group having 1 to 10 carbon atoms such as m-methyl, 3,5-dimethyl or m-ethyl, or an alkoxy group having 1 to 10 carbon atoms such as m-methoxy, 3,5-dimethoxy or m-ethoxy. The three Z groups of the triarylmethyl group, $Z_3C$, may be the same (for example, triphenylmethyl) or different (for example, p-chlorophenyldiphenylmethyl).

The process of the present invention is characterized in that the reaction of methacrylic acid with the triarylmethylating agent is carried out in the presence of an anion exchange resin. The anion exchange resin includes quaternary ammonium type of strongly basic anion exchange resins and tertiary amine type of weakly basic anion exchange resins, and the latter is preferred for the purpose of the present invention. When the quaternary ammonium type of resin is used, there is the possibility that hydrolysis takes place due to an equivalent of water formed from the hydroxide anion and that the polymerization of the starting material and the product takes place owing to its strong basicity. On the contrary, when the tertiary amine type of resin is used, the active group is a weakly basic group such as a tertiary alkylamino or pyridyl group so that there is no fear of hydrolysis or polymerization as mentioned above and the desired ester can be formed by a condensation reaction between the starting materials at an appropriate reaction rate.

Examples of the tertiary amine type of anion exchange resin include commercially available resins such as Amberlite ® IRA45, IRA47, IRA68, IRA93 and IRA94; Amberlyst ® A-21 and A-26; Diaion ® WA-10, WA-11, WA-20, WA-21, WA-30, CR-20 and CR-40; and Dowex ® MWA and WGR.

It is desirable to use an anion exchange resin which is insoluble in an organic solvent used for the reaction in order that the resin can be readily separated from the reaction mixture or repeatedly used. Meanwhile the swelling of the anion exchange resin by the solvent is rather desirable, because soluble impurities are washed off from the resin, the reactivity is increased and the reaction proceeds with good selectivity in a short time to give the desired product as a crystal.

Method of Reaction

Methacrylic acid may be reacted with the triarylmethylating agent in an equivalent ratio. However, it is preferred that methacrylic acid is used in excess of the triarylmethylating agent, for example, in a quantity of 1.5 times by equivalent that of the triarylmethylating agent to completely consume the triarylmethylating agent by the reaction and to prevent byproducts such as triarylmethyl alcohol from being formed. Usually, methacrylic acid is used in a quantity of 1.0 to 1.1 times by equivalent that of the triarylmethylating agent.

The reaction is carried out in an inert organic solvent. The solvent is chosen by taking the solubility of the reactants and the action of the solvent on the anion exchange resin into consideration. For example, when Amberlyst A-21 is used as the anion exchange resin, methylene chloride is preferred as the solvent, since it can swell the resin but not dissolve it and can dissolve the triarylmethylating agent. This solvent scarcely dissolves in water and commercially available methylene chloride contains only a little water so that when the reaction can be terminated in a relatively short time, it is not necessary to dry the methylene chloride solvent prior to the reaction. Other solvents can be chosen from among inert solvents such as acetonitrile or ethyl ether according to the kinds of the anion exchange resins. However, a solvent which can incorporate water dissolved therein such as ethyl ether, is sometimes not preferred, since when the solvent is used for the reaction over a long period of time without preliminary dehydration treatment, there is a possibility that triphenylmethyl alcohol is formed as a by-product.

The simplest reaction mode includes a flow method which comprises passing a solution containing both starting materials through an anion exchange resin layer. Alternatively, a solution of methacrylic acid is first fed to a resin layer to allow the acid to be supported on the resin layer and then the triphenylmethylating agent is passed therethrough to effect the reaction. During the passing of the solution through the resin layer, an ester is formed and flows out, leaving an acid, HX, formed during condensation behind. The reaction time can be controlled by the quantity of the packed resin and the flow velocity of the solution.

The reaction may be carried out batchwise. For example, the solution containing the resin dispersed therein is reacted under stirring. This method often gives results similar to those obtained by the flow method.

The reaction can be carried out at about room temperature, for example, at a temperature of 0° to 50° C. and can be completed within several minutes. If desired, the reaction may be carried out over a wide temperature range of −80° to 100° C. unless any problems of side reactions such as polymerization are caused.

It is necessary that the anion exchange resin has an ion exchange capacity of at least 1 mol per mol of the substrate, and it is preferred to use the resin having an ion exchange capacity of 1 to 20-fold mol, particularly 5 to 10-fold mol.

Action and Effect of the Invention

By carrying out the reaction in the presence of the anion exchange resin, methacrylic acid is rapidly condensed with the triarylmethylating agent in the solution to form a triarylmethyl methacrylate.

A hydroacid HX (for example, hydrohalogenic acid, p-toluenesulfonic acid or perchloric acid) of a group thereby eliminated in the reaction forms a salt with the anion exchange resin to become insoluble so that the hydrolysis of the produced ester can be minimized even in the presence of some water in the system. Since the reaction solution separated from the solid resin does not contain any salts formed by the condensation, crude crystal of the desired triarylmethyl methacrylate can be obtained in a high yield merely by distilling off the solvent.

Thus, the process of the present invention only slightly suffers side reactions and the salt formed by the condensation can be separated of itself in the form of a resin salt from the reaction solution so that the ester can be easily obtained in the pure form by crystallization. Accordingly the process of the present invention can dispense with purifying treatments by, for example, chromatography which sometimes causes hydrolysis.

The anion exchange resin used as a condensing agent can be easily regenerated by washing it with an alkali and be used repeatedly. Thus, the present invention is also in this respect superior to the prior art processes where a metal salt or a low-molecular amine is used.

It has been found that the process of the present invention can be accomplished only by a specific combination wherein methacrylic acid is used as a carboxylic acid component and the triarylmethyl group is used as a tertiary alcohol component. When an acyclic compound such as t-butyl bromide or chloride is used as the tertiary alcohol component, the compound does not react with methacrylic acid. When acrylic or acetic acid is used as the carboxylic acid component, only a trace quantity of the triphenylmethyl ester is formed. Accordingly, it is an unexpected finding that methacrylic acid is rapidly condensed with the triarylmethylating agent in the presence of the anion exchange resin and the desired product can be obtained in the form of crystal only by distilling off the solvent from the reaction solution.

The following examples will further illustrate the present invention.

The NMR and IR data in the examples were determined by the following methods. The $^1$H NMR spectrum was measured using TMS as internal reference by JEOL JNM-NH-100. The IR spectrum was measured by JASCO IRA-2.

EXAMPLE 1

5.05 g (0.05 mol) of dry triethylamine distilled in the presence of calcium hydride was added to 20 ml of anhydrous ether distilled in the presence of lithium aluminum hydride, and the mixture was cooled with ice in a nitrogen atmosphere. 0.86 g (0.01 mol) of methacrylic acid was added thereto and the mixture was stirred. While cooling the mixture with ice, 3.23 g (0.01 mol) of triphenylmethyl bromide dissolved in 10 ml of anhydrous ether was added thereto, whereby the reaction rapidly proceeded and triethylamine hydrobromide was precipitated. The reaction was continued for 2.5 hr until the salt was completely precipitated, and the resulting crystal was recovered by filtration. When the solvent and excess triethylamine were distilled off, triphenylmethyl methacrylate was obtained as a crystal, which was then recrystallized from ether to give 3.07 g (yield: 92.9%) of a colorless prismatic crystal.

m.p.: 100°–101° C. (Lit.: 101°–102° C.);
IR (C Cl$_4$): 1725, 1490, 1140 cm$^{-1}$;
$^1$HNMR (CDCl$_3$): δ 1.99 (3H, dd, J=1.0, 1.4 H$_z$), 5.60 (1H, m) 6.23 (1H, m), 7.2–7.5 (15H, m);
MS: m/z 328 (M$^+$).

EXAMPLE 2

The procedure of Example 1 was repeated except that the reaction was carried out in dry THF at room temperature. 3.20 g (yield: 96.8%) of triphenylmethyl methacrylate was obtained.

EXAMPLE 3

The procedure of Example 2 was repeated except that 2.79 g (0.01 mol) of triphenylmethyl chloride was used. 3.03 g (yield: 91.7%) of triphenylmethyl methacrylate was obtained.

EXAMPLE 4

The procedure of Example 2 was repeated except that 3.96 g (0.05 mol) of dry pyridine was used in place of triethylamine and the reaction was carried out in THF. It was confirmed when the reaction solution was examined by means of thin-layer chromatography that triphenylmethyl methacrylate was quantitatively formed. After the amine salt was removed by filtration, the solvent and excess pyridine were evaporated. The intended product was obtained as a syrup. An attempt to recrystallize it from ether and n-hexane failed, since hydrolysis took place due to water contained in the solvents for recrystallization and triphenylmethyl alcohol was formed.

EXAMPLE 5

The procedure of Example 4 was repeated except that 2.79 g of triphenylmethyl chloride was used. The intended product was quantitatively formed and separated a syrup, which was then recrystallized from a thoroughly dried solvent. A crystal similar to that of Example 1 was obtained.

EXAMPLE 6

For the purpose of comparison, 1.01 g (equivalent) of triethylamine was used and an experiment similar to that described in Example 1 was carried out. The concentrate obtained by filtering the amine salt and evaporating the solvent contained triphenylmethyl alcohol, and the intended product having a high purity similar to that of the product of Example 1 could not be obtained.

EXAMPLE 7

10 g, containing 0.0047–0.005 gram of the active group per gram of the resin, on a dry basis, of Amberlyst ® A-21 as a weakly basic anion exchange resin was weighed and washed with methanol and acetone to remove water.

The resin was then dispersed in 20 ml of methylene chloride to swell it, and then 0.86 g (0.01 mol) of methacrylic acid was added thereto. The mixture was stirred at room temperature. 3.23 g (0.01 mol) of triphenylmethyl bromide dissolved in 20 ml of methylene chloride was added thereto. The reaction was terminated within 10 minutes.

The resin was removed by filtration and the solvent was distilled off from the reaction solution, whereby the intended product was obtained as a crude crystal. The product was recrystallized from ether to give 3.12 g (yield: 94.5%) of triphenylmethyl methacrylate as a colorless prismatic crystal.

M.P.: 100°~101° C. (Lit. 101°~102° C.).

IR(CCl$_4$) 1725, 1490, 1140 cm$^{-1}$.

$^1$H NMR(CDCl$_3$): δ1.99(3H, dd, J=1.0, 1.4 Hz , 5.60 (1H, m) 6.23(1H, m), 7.2~7.5(15H, m).

MS: m/z 328(M$^+$).

EXAMPLE 8

The procedure of Example 7 was repeated except that 2.37 g (0.0085 mol) of triphenylmethyl chloride was used in place of triphenylmethyl bromide. 2.26 g (yield: 80.4%) of triphenylmethyl methacrylate was obtained.

EXAMPLE 9

The same starting materials as those of Example 8 were used and the reaction was carried out in ether (not previously dehydrated) as the solvent. The resin was immersed in ether overnight, but did not swell unlike the immersion in methylene chloride and the reaction required a long time.

Ether was evaporated from the reaction solution to obtain a crystal which was triphenylmethyl alcohol (yield: 50.9%). Triphenylmethyl methacrylate (yield: 28.7%) was obtained from the mother liquor.

EXAMPLE 10

A glass column of 1.5 cm in diameter and 25 cm in height was packed with 20 g of Amberlyst ® A-21 and the packed layer was wetted with 20 ml of methylene chloride. A solution of a substrate composed of 0.86 g (0.01 mol) of methacrylic acid and 3.23 g (0.01 mol) of triphenylmethyl bromide dissolved in 20 ml of methylene chloride was passed through the layer downward over a period of 30 min.

Methylene chloride was distilled off from the effluent to obtain 2.90 g (yield: 87.9%) of triphenylmethyl methacrylate as a crude crystal. The product was recrystallized from ether to give 2.79 g (yield: 84.4%) of the pure crystal.

EXAMPLE 11

The procedure of the flow method of Example 10 was repeated except that 2.79 g (0.01 mol) of triphenylmethyl chloride was used in place of triphenylmethyl bromide. After recrystallization, 2.84 g (yield: 86.1%) of triphenylmethyl methacrylate was obtained.

EXAMPLE 12

The anion exchange resin used in Example 7 was regenerated by washing with 500 ml of a 4% aqueous caustic soda solution and then with methanol and acetonitrile to remove water. 0.43 g (0.005 mol) of methacrylic acid and 1.39 g (0.005 mol) of triphenylmethyl chloride were dissolved in methylene chloride and reacted together batchwise in the presence of the above regenerated resin to give 1.59 g (yield: 96.0%) of triphenylmethyl methacrylate.

EXAMPLE 13

The procedure of each of Examples 7 and 8 was repeated except that 0.01 mol of acrylic acid was used in place of methacrylic acid. Only a trace quantity of triphenylmethyl acrylate was formed.

The procedure of Example 7 was repeated except that 0.01 mol of acetic acid was used. Only a trace quantity of triphenylmethyl acetate was formed.

EXAMPLE 14

The procedure of Example 7 was repeated except that 0.01 mol of t-butyl bromide was used in place of triphenylmethyl bromide. However, no reaction took place. t-Butyl chloride gave a similar result.

The embodiments of the invention in which an exclusive property or privilege is claimed are defined as follows:

1. A process for preparing a triarylmethyl methacrylate having the formula

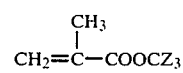

wherein Z is aryl and the three Z groups can be the same or different, which consists essentially of:
reacting methacrylic acid with a triarylmethylating agent Z$_3$C.X, according to the reaction scheme

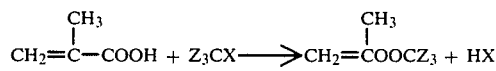

wherein X is a group that is reactable with the hydrogen of the carboxyl group of methacrylic acid, the reaction being carried out in the presence of a tertiary amine weakly basic anion exchange resin and in an anhydrous, inert organic solvent which does not dissolve the anion exchange resin, said anion exchange resin being capable of removing said HX from the reaction mixture, the amount of said methacrylic acid being in the range of from 1.0 to 1.5 equivalents relative to said triarylmethylating agent; separating the anion exchange resin containing HX from the reaction mixture; then distilling off said solvent; and recovering said triarylmethyl methacrylate.

2. The process as claimed in claim 1, in which X is selected from the group consisting of halogen, —O-SO$_2$C$_6$H$_4$CH$_3$, —OSO$_2$CH$_3$, —ClO$_4$, —CN and —SCN.

3. The process as claimed in claim 1 in which Z is

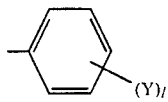

wherein l is an integer of 0 to 5 and Y is alkyl having 1 to 10 carbon atoms, alkoxy having 1 to 10 carbon atoms or halogen.

4. The process as claimed in claim 1, in which said triarylmethylating agent is triphenylmethylchloride or triphenylmethylbromide.

5. The process as claimed in claim 1 in which said anion exchange resin is insoluble in but is capable of being swelled by said solvent.

* * * * *